United States Patent
Tseng et al.

(10) Patent No.: US 10,557,795 B2
(45) Date of Patent: Feb. 11, 2020

(54) METAL ION DETECTION EQUIPMENT AND METAL ION DETECTION METHOD

(71) Applicant: National Tsing Hua University, Hsinchu (TW)

(72) Inventors: Fan-Gang Tseng, Taipei (TW); Jen-Kuei Wu, New Taipei (TW); Jian Ren Lai, Changhua County (TW)

(73) Assignee: National Tsing Hua University, Hsinchu (TW)

( * ) Notice: Subject to any disclaimer, the term of this patent is extended or adjusted under 35 U.S.C. 154(b) by 442 days.

(21) Appl. No.: 15/369,353

(22) Filed: Dec. 5, 2016

(65) Prior Publication Data

US 2018/0059017 A1 Mar. 1, 2018

(30) Foreign Application Priority Data

Aug. 31, 2016 (TW) .............................. 105128143 A

(51) Int. Cl.
| | | |
|---|---|---|
| *G01N 21/47* | (2006.01) | |
| *B01J 19/08* | (2006.01) | |
| *G01N 33/18* | (2006.01) | |
| *G01N 21/77* | (2006.01) | |

(52) U.S. Cl.
CPC ........ *G01N 21/4738* (2013.01); *B01J 19/088* (2013.01); *G01N 21/7746* (2013.01); *G01N 33/18* (2013.01); *B01J 2219/0801* (2013.01); *B01J 2219/0809* (2013.01);
(Continued)

(58) Field of Classification Search
CPC ........ B01J 2219/0809; B01J 2219/0801; B01J 2219/0815; B01J 2219/0877; B01J 19/088; G01N 21/4738; G01N 21/7746; G01N 33/18; G01N 33/1813; G01N 2021/87773;
(Continued)

(56) References Cited

U.S. PATENT DOCUMENTS 6,270,650 B1 * 8/2001 Kazi ................... C02F 1/46104
204/242
6,897,965 B2 5/2005 Ghadiri et al.
(Continued)

FOREIGN PATENT DOCUMENTS

| CN | 101710118 | 5/2010 |
|---|---|---|
| CN | 102313717 | 8/2013 |
| CN | 103979543 | 12/2015 |

(Continued)

OTHER PUBLICATIONS

Lai et al., Transducers 2015, Jun. 21-25, 2015.*
(Continued)

*Primary Examiner* — Gurpreet Kaur
(74) *Attorney, Agent, or Firm* — J.C. Patents

(57) ABSTRACT

A metal ion detection equipment and a metal ion detection method are provided. The metal ion detection equipment includes a porous silicon resonant cavity structure, an electrochemical device and a spectrum detecting device. A sample solution permeates into the porous silicon resonant cavity structure. A to-be-detected metal ion of the sample solution in the porous silicon resonant cavity structure is reduced into a to-be-detected metal by the electrochemical device. The spectrum detecting device detects a spectral variation of a reflective light from the porous silicon resonant cavity structure.

18 Claims, 7 Drawing Sheets

(52) U.S. Cl.
CPC .............. *B01J 2219/0815* (2013.01); *B01J 2219/0877* (2013.01); *G01N 2021/7726* (2013.01); *G01N 2201/12* (2013.01)

(58) Field of Classification Search
CPC ... G01N 2021/7776; G01N 2021/7789; G01N 2021/558; G01N 2021/12; G01N 2021/436
See application file for complete search history.

(56) References Cited

U.S. PATENT DOCUMENTS

| | | | |
|---|---|---|---|
| 7,330,252 | B2 | 2/2008 | Koo et al. |
| 2004/0161369 | A1* | 8/2004 | Chan .............. B01D 67/0062 422/82.05 |

FOREIGN PATENT DOCUMENTS

| | | |
|---|---|---|
| CN | 105891167 | 8/2016 |
| TW | 200837343 | 9/2008 |
| TW | 200918893 | 5/2009 |
| TW | 200935049 | 8/2009 |
| TW | 201608230 | 3/2016 |

OTHER PUBLICATIONS

Maniya et al. Optik, 125, 828-831 (Year: 2014).*
Harraz, Sensors and Actuators B: Chemical, 202, 897-912 (Year: 2014).*
"Office Action of Taiwan Counterpart Application," dated Feb. 6, 2017, p. 1-p. 4.
Huimin Ouyang, et al., "Macroporous Silicon Microcavities for Macromolecule Detection," Advanced Functional Materials, vol. 15, No. 11, Nov. 2005, pp. 1851-1859.
Hongyan Zhang, et al., "Surface layer reflective index changes of Au nanoparticle functionalized porous silicon microcavity for DNA detection," Current Applied Physics, vol. 15, No. 8, Aug. 2015, pp. 870-876.
Minh-Hang Nguyen, et al., "Cascaded nano-porous silicon for high sensitive biosensing and functional group distinguishing by Mid-IR spectra" Biosensors and Bioelectronics, vol. 47, Sep. 15, 2013, pp. 80-85.

* cited by examiner

METAL ION DETECTION EQUIPMENT AND METAL ION DETECTION METHOD

CROSS-REFERENCE TO RELATED APPLICATION

This application claims the priority benefit of Taiwan application serial no. 105128143, filed on Aug. 31, 2016. The entirety of the above-mentioned patent application is hereby incorporated by reference herein and made a part of this specification.

BACKGROUND OF THE INVENTION

Field of the Invention

The invention relates to a detection equipment and a detection method, and particularly relates to a metal ion detection equipment and a metal ion detection method.

Description of Related Art

In the traditional heavy metal detection and analysis process, mainly, the high performance liquid chromatography (HPLC) is performed to remove the microorganisms and other impurities in water, and the mass spectrometry analysis such as the inductively coupled plasma mass spectrometry (IPC-MS) or the flame atomic absorption spectrometry (FLAA) is performed to analyze the types and concentrations of heavy metals. However, in the heavy metal microanalysis, different elements may interfere with each other, so that the pre-processing of the analysis needs to be performed by professionals. The process is complicated and time consuming, and the analysis method has considerable operator error. Therefore, the training of the professionals and the time consuming operation process become the biggest issue. In addition, the above instruments are more sophisticated and large-scale equipment, so the problems of uncommon detection mechanism, high cost and incapability of instant detection are caused.

Furthermore, the current metal detecting component uses the combination of the protein with high selectivity or synthetic molecule and to-be-detected heavy metal ion to produce the change of the fluorescence or electrochemical signal, so as to achieve the effect of detection. However, only the single element analysis can be performed in the heavy metal sensors of this kind. In addition, the electrochemical analysis can be used to detect heavy metal. For example, the adsorption stripping voltammetry (ASV) can be used to increase the signal of cyclic voltammetry, and different working electrodes can be incorporated to analyze different heavy metals. Although the above methods can achieve the effect of signal increasing, the analyzing process is too long and the instant detection can't be performed.

Therefore, the development of a metal ion detection equipment capable of instant detection and having excellent detection limit is a problem that the researchers are eager to solve.

SUMMARY OF THE INVENTION

The present invention provides a metal ion detection equipment, which has excellent performance of excellent detection limit and high accuracy.

The present invention provides a metal ion detection method, which is capable of instant detection and effectively improving detection limit.

The present invention provides a metal ion detection equipment, including a porous silicon resonant cavity structure, an electrochemical device, and a spectrum detecting device. A sample solution permeates into the porous silicon resonant cavity structure. The electrochemical device reduces a to-be-detected metal ion of the sample solution in the porous silicon resonant cavity structure into a to-be-detected metal. The spectrum detecting device detects a spectral variation of the reflective light from the porous silicon resonant cavity structure.

In an embodiment of the invention, the porous silicon resonant cavity structure includes a first bragg reflector, a second bragg reflector, and a defect layer located between the first bragg reflector and the second bragg reflector, wherein the first bragg reflector and the second bragg reflector both include a plurality of low refractive index layers and a plurality of high refractive index layers, and the low refractive index layer and the high refractive index layer are arranged alternately.

In an embodiment of the invention, a thickness of the low refractive index layer is 100 nm to 200 nm, for example.

In an embodiment of the invention, a thickness of the high refractive index layer is 50 nm to 100 nm, for example.

In an embodiment of the invention, a ratio of the thickness of the defect layer to the high refractive index layer is 1.5 to 2.5, for example.

In an embodiment of the invention, a refractive index of the low refractive index layer is 1.1 to 1.3, for example.

In an embodiment of the invention, a refractive index of the high refractive index layer is 1.5 to 1.7, for example.

In an embodiment of the invention, a refractive index of the defect layer is 1.5 to 1.7, for example.

In an embodiment of the invention, the electrochemical device can include a reaction chamber, a working electrode, a counter electrode, and a potentiostat. The reaction chamber is configured to load the sample solution. The working electrode and the counter electrode are disposed in the reaction chamber, and the porous silicon resonant cavity structure is disposed on the working electrode. The potentiostat is connected to the working electrode and the counter electrode.

In an embodiment of the invention, the electrochemical device further includes a reference electrode. The reference electrode is disposed in the reaction chamber and connected to the potentiostat.

The present invention provides a metal ion detection method, which includes the following steps. A to-be-detected metal ion of a sample solution in a porous silicon resonant cavity structure is reduced into a to-be-detected metal. A spectral variation of a reflective light from the porous silicon resonant cavity structure is detected.

In an embodiment of the invention, the porous silicon resonant cavity structure includes a first bragg reflector, a second bragg reflector, and a defect layer located between the first bragg reflector and the second bragg reflector, wherein the first bragg reflector and the second bragg reflector both include a plurality of low refractive index layers and a plurality of high refractive index layers, and the low refractive index layer and the high refractive index layer are arranged alternately.

In an embodiment of the invention, an electrochemical device can be configured to reduce the to-be-detected metal ion into the to-be-detected metal.

In an embodiment of the invention, the sample solution includes a variety of metal ions, and before the to-be-detected metal ion is reduced into the to-be-detected metal, the metal ion detection method further includes using the electrochemical device to reduce a metal ion with a reduction potential higher than a reduction potential of the to-be-detected metal ion into a metal.

In an embodiment of the invention, the electrochemical device can include a reaction chamber, a working electrode, a counter electrode, and a potentiostat. The reaction chamber is configured to load the sample solution. The working electrode and the counter electrode are disposed in the reaction chamber, and the porous silicon resonant cavity structure is disposed on the working electrode. The potentiostat is connected to the working electrode and the counter electrode.

In an embodiment of the invention, a step of reducing the metal ion with the reduction potential higher than the reduction potential of the to-be-detected metal ion into the metal includes the following steps. The porous silicon resonant cavity structure is disposed in the electrochemical device. The sample solution is rendered to permeate into the porous silicon resonant cavity structure. A voltage is applied on the working electrode and the counter electrode, so that the metal ion with the reduction potential higher than the reduction potential of the to-be-detected metal ion is reduced into the metal.

In an embodiment of the invention, a step of reducing the to-be-detected metal ion of the sample solution in the porous silicon resonant cavity structure into the to-be-detected metal can include the following steps. The porous silicon resonant cavity structure is disposed in the electrochemical device. The sample solution permeates into the porous silicon resonant cavity structure. A voltage is applied on the working electrode and the counter electrode, so that the to-be-detected metal ion is reduced into the to-be-detected metal.

In an embodiment of the invention, after the metal ion with the reduction potential higher than the reduction potential of the to-be-detected metal ion is reduced into the metal, and before the to-be-detected metal ion is reduced into the to-be-detected metal, the metal ion detection method further includes detecting a spectrum of a reflective light from the porous silicon resonant cavity structure.

In an embodiment of the invention, a spectrum analyzer is configured to detect the spectral variation.

In an embodiment of the invention, a step of detecting the spectral variation of the reflective light from the porous silicon resonant cavity structure can include the following steps. An incident light is provided to the porous silicon resonant cavity structure with the to-be-detected metal reduced therein, so as to produce a reflective light signal. The reflective light signal from the porous silicon resonant cavity structure is received.

In an embodiment of the invention, a method of detecting the spectral variation is an in-situ detection or an ex-situ detection, for example.

Based on the above, in the metal ion detection equipment and method provided by the present invention, through the reduction of the to-be-detected metal ion in the porous silicon resonant cavity structure into the to-be-detected metal, the relatively greater change of the refractive index can be caused, so that the detection limit can be improved.

In addition, in the metal ion detection equipment and method provided by the present invention, metal ion can be selected according to the reduction potential of the metal ion. Therefore, no additional process is needed to remove the non-to-be-detected metal ion in the sample solution, so that it is benefit to perform target molecule selection, instant detection and detection process simplification.

Furthermore, the porous silicon resonant cavity structure in the metal ion detection equipment of the invention has the advantage such as large surface area and high sensitivity, also, the production thereof is easy, and the cost thereof is low.

To make the above features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
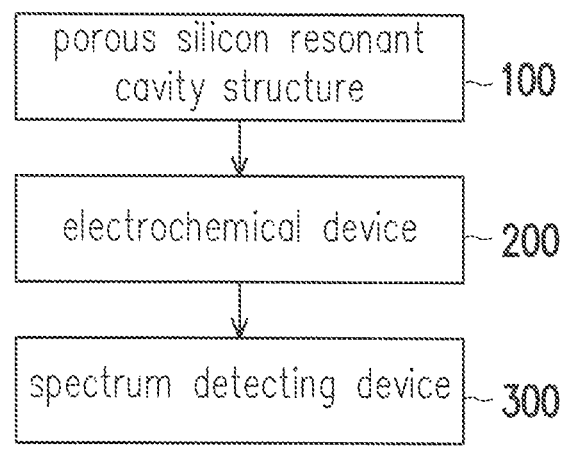
FIG. 1 is a block diagram illustrating the metal ion detection equipment of an embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a block diagram illustrating the metal ion detection equipment of an embodiment of the present invention.

Referring to FIG. 1, the metal ion detection equipment 10 of the invention includes a porous silicon resonant cavity structure 100, an electrochemical device 200, and a spectrum detecting device 300. In the process of metal ion detection, the porous silicon resonant cavity structure 100 is placed in the electrochemical device 200, and the sample solution in the electrochemical device 200 may permeate into the porous silicon resonant cavity structure 100. The electrochemical device 200 can reduce a to-be-detected metal ion of the sample solution in the porous silicon resonant cavity structure 100 into a to-be-detected metal. Thereafter, a spectrum detecting device 300 can be configured to detect a spectral variation of a reflective light from the porous silicon resonant cavity structure 100, so that the metal ion is detected by the spectral variation.

In the embodiment, the spectrum detecting device 300 is the general spectrum analyzer, micro-spectrum analyzer or small-scale spectrum analyzer, for example. And the body, light source, optical element constituting the spectrum detecting device 300 are all generally knowledge in the field, and will not be repeated herein. The spectral variation of the reflective light from the porous silicon resonant cavity structure 100 can be detected by the spectrum detecting device 300.

Figure 2:
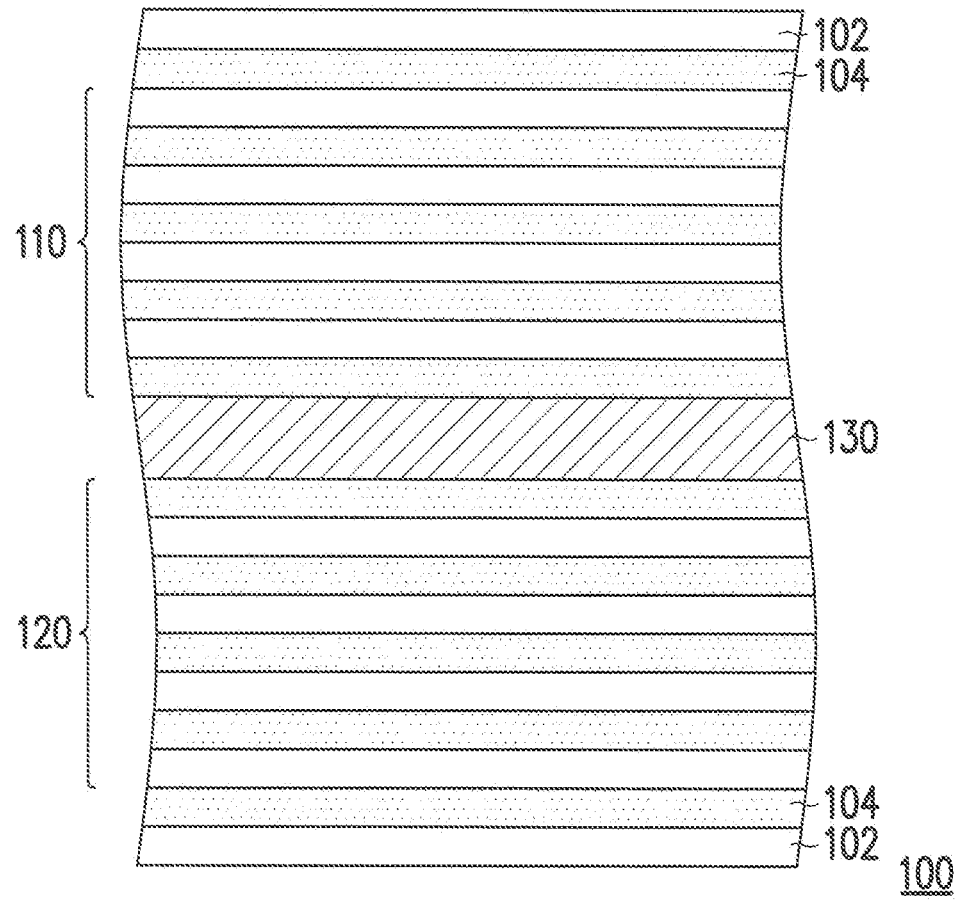
FIG. 2 is a schematic diagram of the porous silicon resonant cavity structure according to an embodiment of the present invention.

FIG. 2 is a schematic diagram of the porous silicon resonant cavity structure according to an embodiment of the present invention.

Referring to FIG. 2, the porous silicon resonant cavity structure 100 includes a first bragg reflector 110, a second bragg reflector 120, and a defect layer 130, wherein the defect layer 130 is located between the first bragg reflector 110 and the second bragg reflector 120.

The first bragg reflector 110 and the second bragg reflector 120 both include a plurality of high refractive index layers 102 and a plurality of low refractive index layers 104, and the high refractive index layer 102 and the low refractive index layer 104 are arranged alternately. In the embodiment, the first bragg reflector 110 and the second bragg reflector 120 both include 5 high refractive index layers 102 and 5 low refractive index layers 104, but the invention is not limited thereto. According to the demand, people with ordinary skill in the art can determine the number of the high refractive index layer 102 and the low refractive index layer 104, even the alternate order thereof.

In the embodiment, the porous silicon resonant cavity structure is produced through performing the electrochemical etching on p-type silicon substrate, for example. Specifically, the high refractive index layer 102, low refractive index layer 104, and the defect layer 130 of the porous silicon resonant cavity structure 100 can be formed through the electrochemical etching of different value of current density. The etching solution in the electrochemical etching is formed by mixing the 49% hydrofluoric acid and 99.5% alcohol in the volume ratio of 3:7, for example. The high refractive index layer 102 is formed by etching with current density of 10 mA/cm$^2$, for example. The low refractive index layer 104 is formed by etching with current density of 30 mA/cm$^2$, for example. The defect layer 130 is formed by etching with current density of 10 mA/cm$^2$, for example.

The refractive index of the high refractive index layer 102, low refractive index layer 104, and the defect layer 130 is related to the current density applied during the process of electrochemical etching. Specifically, during the process of electrochemical etching, the higher the applied current density, the larger the pore size of the porous silicon layer formed by etching. And, the larger the pore size of the porous silicon layer, the lower the refractive index. Therefore, the refractive index of the high refractive index layer 102, low refractive index layer 104, and the defect layer 130 can be adjusted through controlling the value of the current density. In the embodiment, a refractive index of the high refractive index layer 102 is 1.5 to 1.7, for example. A refractive index of the low refractive index layer 104 is 1.1 to 1.3, for example. A refractive index of the defect layer 130 is 1.5 to 1.7, for example.

In addition, the porous silicon layer of different thickness can be obtained through controlling the etching time. In an embodiment of the invention, a thickness of the high refractive index layer 102 is 50 nm to 100 nm, for example. A thickness of the low refractive index layer 104 is 100 nm to 200 nm, for example. And, a thickness ratio of the thickness of the defect layer 130 to the thickness of the high refractive index layer 102 is 1.5 to 2.5, for example. In a preferred embodiment, a thickness ratio of the thickness of the defect layer 130 to the thickness of the high refractive index layer 102 is about 2:1.

In the embodiment, a hydrophilic treatment can further be performed on the porous silicon resonant cavity structure 100, so that the porous silicon resonant cavity structure 100 is hydrophilic. The hydrophilic treatment can be, for example, immersing the produced porous silicon resonant cavity structure 100 in alcohol for 10 minutes, followed by immersing in 6M sulfuric acid for 40 minutes, making the silicon surface of the porous silicon resonant cavity structure 100 hydrophilic, so as to aid the solution to immerse into the porous silicon resonant cavity structure quickly.

Due to the porous characteristic of the porous silicon resonant cavity structure 100, the porous silicon resonant cavity structure 100 has higher surface area, and the detection range is aided to be increased. In addition, the porous silicon resonant cavity structure 100 is a structure having photonic crystal. Therefore, the oscillating field of the photonic crystal is configured to interact with the target molecule, so as to increase the detection sensitivity.

In addition, the porous silicon resonant cavity structure 100 is an optic resonant cavity structure sensitive to the refractive index, wherein the defect layer 130 located between the first bragg reflector 110 and the second bragg reflector 120 may induce an extremely narrow characteristic peak in the high reflection band of the reflective light spectrum. The characteristic peak is a sensitive parameter, and the wavelength corresponding to the characteristic peak is affected by the refractive index of the defect layer 130. Therefore, after the sample solution immersed into the porous silicon resonant cavity structure 100 (especially the defect layer 130), the overall refractive index is changed, so as to make the characteristic peak shifted. In addition, the higher the concentration of the target molecule, the greater the shifted value of the characteristic peak. Therefore, the concentration of the target molecule in the solution can be calculated according to the shifted value of the characteristic peak.

In the embodiment, the target molecule is the metal ion in the liquid sample, for example. The concentration of the target molecule is 0.1 ppb to 1000 ppb, for example. In the case of the cadmium nitrate solution, for example, the detection limit of the invention can be less than 1 ppb.

Figure 3:
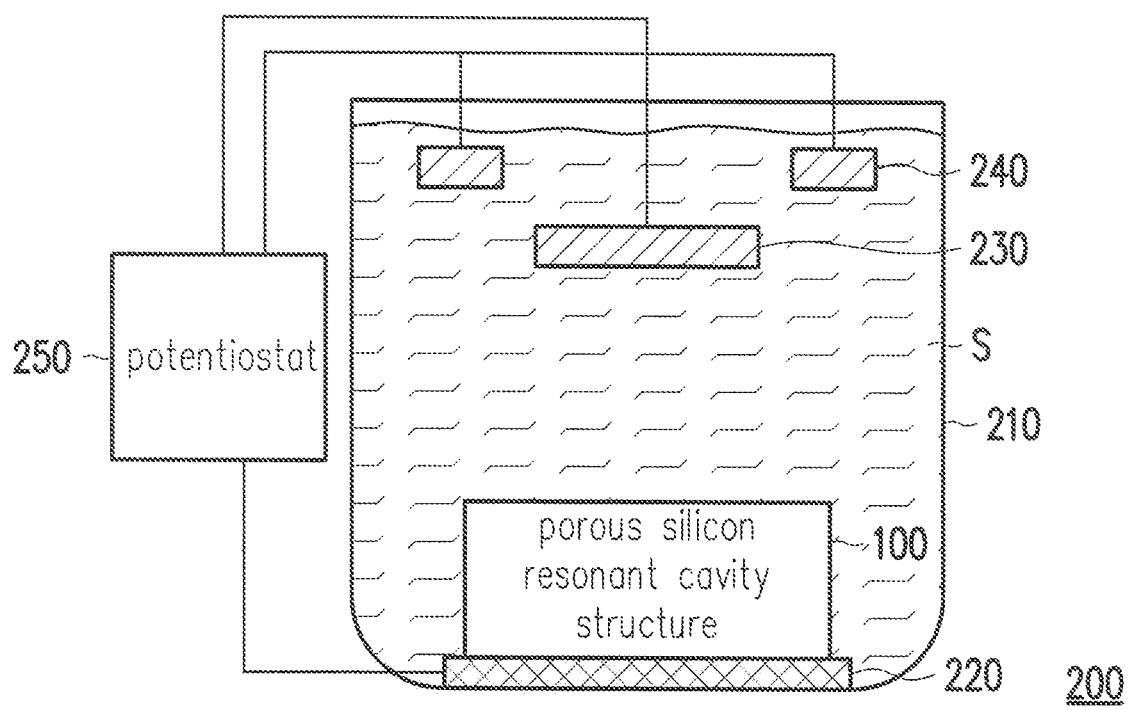
FIG. 3 is a schematic diagram of the electrochemical device according to an embodiment of the present invention.

FIG. 3 is a schematic diagram of the electrochemical device according to an embodiment of the present invention.

Referring to FIG. 3, the electrochemical device 200 of the embodiment includes a reaction chamber 210 configured to load the sample solution S, a working electrode 220, a counter electrode 230, and a potentiostat 250. The electrochemical device 200 can be configured to perform the electrochemical oxidation-reduction reaction. The working electrode 220 and the counter electrode 230 are disposed in the reaction chamber 210, and the potentiostat 250 is connected to the working electrode 220 and the counter electrode 230. The process of performing the electrochemical oxidation-reduction reaction, the porous silicon resonant cavity structure 100 is disposed on the working electrode 220, and a voltage is applied on the working electrode 220 and the counter electrode 230 by the potentiostat 250, so that the to-be-detected metal ion in the sample solution S are reduced into the to-be-detected metal.

In the embodiment, the electrochemical device 200 can further includes a reference electrode 240. The reference electrode 240 is disposed in the reaction chamber 210 and connected to the potentiostat 250. The reference electrode 240 can aid to increase the accuracy and stability of the applied voltage. In the embodiment, the position and number of the working electrode 220, counter electrode 230, and reference electrode 240 are only for the purpose of reference, the invention is not limited thereto. Person having ordinary skill in the art can change the position and number of the working electrode 220, counter electrode 230, and reference electrode 240 according to the demand.

Figure 4:
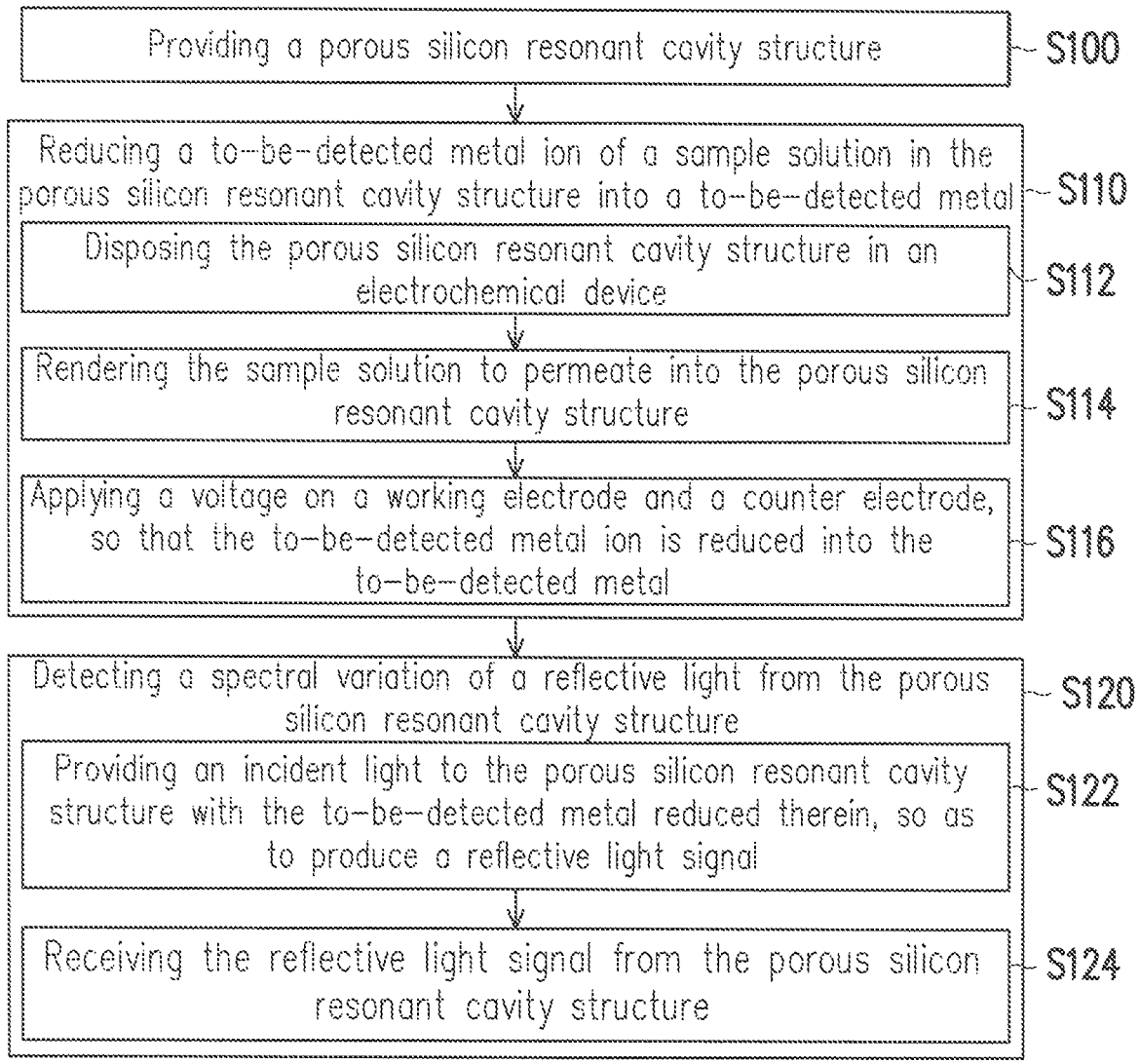
FIG. 4 is a flow chart illustrating the metal ion detection according to the first embodiment of the present invention.

FIG. 4 is a flow chart illustrating the metal ion detection according to the first embodiment of the present invention.

Referring to FIG. 4, the specific description of the steps of the metal ion detection are provided in the following paragraphs.

First, the step S100 is performed: a porous silicon resonant cavity structure is provided. In the embodiment, the porous silicon resonant cavity structure 100 in FIG. 2 is used, for example. The structure related to the porous silicon resonant cavity structure 100 are described in detail in the above embodiments, and will not be repeated herein.

Then, the step S110 is performed: a to-be-detected metal ion of a sample solution in the porous silicon resonant cavity structure is reduced into a to-be-detected metal. The step S110 can further include sub-steps S112, S114, S116. The sub-step S112 is performed: the porous silicon resonant cavity structure is disposed in an electrochemical device. In the embodiment, the electrochemical device 200 in FIG. 3 is used, for example. The porous silicon resonant cavity structure is disposed on a working electrode. The structure related to the electrochemical device 200 are described in detail in the above embodiments, and will not be repeated herein.

Then, the sub-step S114 is performed: the sample solution is rendered to permeate into the porous silicon resonant cavity structure. Specifically, the sample solution is injected into a reaction chamber of the electrochemical device, so that the sample solution covers the whole porous silicon resonant cavity structure and permeates into the porous silicon resonant cavity structure.

Then, the sub-step S116 is performed: a voltage is applied on a working electrode and a counter electrode, so that the to-be-detected metal ion is reduced into the to-be-detected metal. Specifically, the voltage is applied on the working electrode and the counter electrode through a potentiostat, so that the to-be-detected metal ion in the sample solution is reduced into the to-be-detected metal, and the reduced to-be-detected metal will be adsorbed on a surface and in the pores of the porous silicon resonant cavity structure. In the embodiment, the time of applying the voltage is 10 minutes to 40 minutes.

Thereafter, the step S120 is performed: a spectral variation of a reflective light from the porous silicon resonant cavity structure is detected. In the embodiment, a method of detecting the spectral variation is in-situ detection. That is, the spectral variation of the porous silicon resonant cavity structure in the electrochemical device is directly detected with a spectrum analyzer. In another embodiment, a method of detecting the spectral variation is ex-situ detection. That is, the porous silicon resonant cavity structure is taken out from the electrochemical device first, then the spectrum analyzer is used to detect the above spectral variation. The step S120 can further include sub-steps S122, S124. The sub-step S122 is performed: an incident light is provided to the porous silicon resonant cavity structure with the to-be-detected metal reduced therein, so as to produce a reflective light signal. Specifically, an incident light is provided to the porous silicon resonant cavity structure with the to-be-detected metal reduced therein by a light source, so as to produce a reflective light signal. The wavelength of the incident light is 360 nm to 2400 nm, for example.

Then, the sub-step S124 is performed: a reflective light signal from the porous silicon resonant cavity structure is received, and the reflective light spectral variation is displayed through a computer analysis. The concentration of the to-be-detected metal can be calculated according to the sifted value of the reflective light spectrum (that is, the shifted value of the characteristic peak). In the method of in-situ detection, before the execution of the sub-step S116, a spectrum of the reflective light from the porous silicon resonant cavity structure is detected first. Specifically, before the to-be-detected metal ion in the sample solution is reduced into the to-be-detected metal, the spectrum analyzer is used to detect the spectrum of the porous silicon resonant cavity structure first, so as to be used as a blank spectrum for the following detection of the spectral variation. In the method of the ex-situ detection, the reflective light spectrum of the porous silicon resonant cavity structure injected with deionized water is used as the blank spectrum.

It can be known from the above embodiment that because the porous silicon resonant cavity structure is a photonic crystal structure of porous silicon, and has high surface area, so the detection range can be increased. In addition, the oscillating field of the photonic crystal can be used by the porous silicon resonant cavity structure to interact with the to-be-detected metal, so as to increase the detection sensitivity. Furthermore, in the embodiment, through the reduction of the to-be-detected metal ion in the porous silicon resonant cavity structure into the to-be-detected metal, the relatively greater change of the refractive index (relative to the change of the refractive index caused by the to-be-detected metal ion) can be caused, so that the detection limit can be improved.

Figure 5:
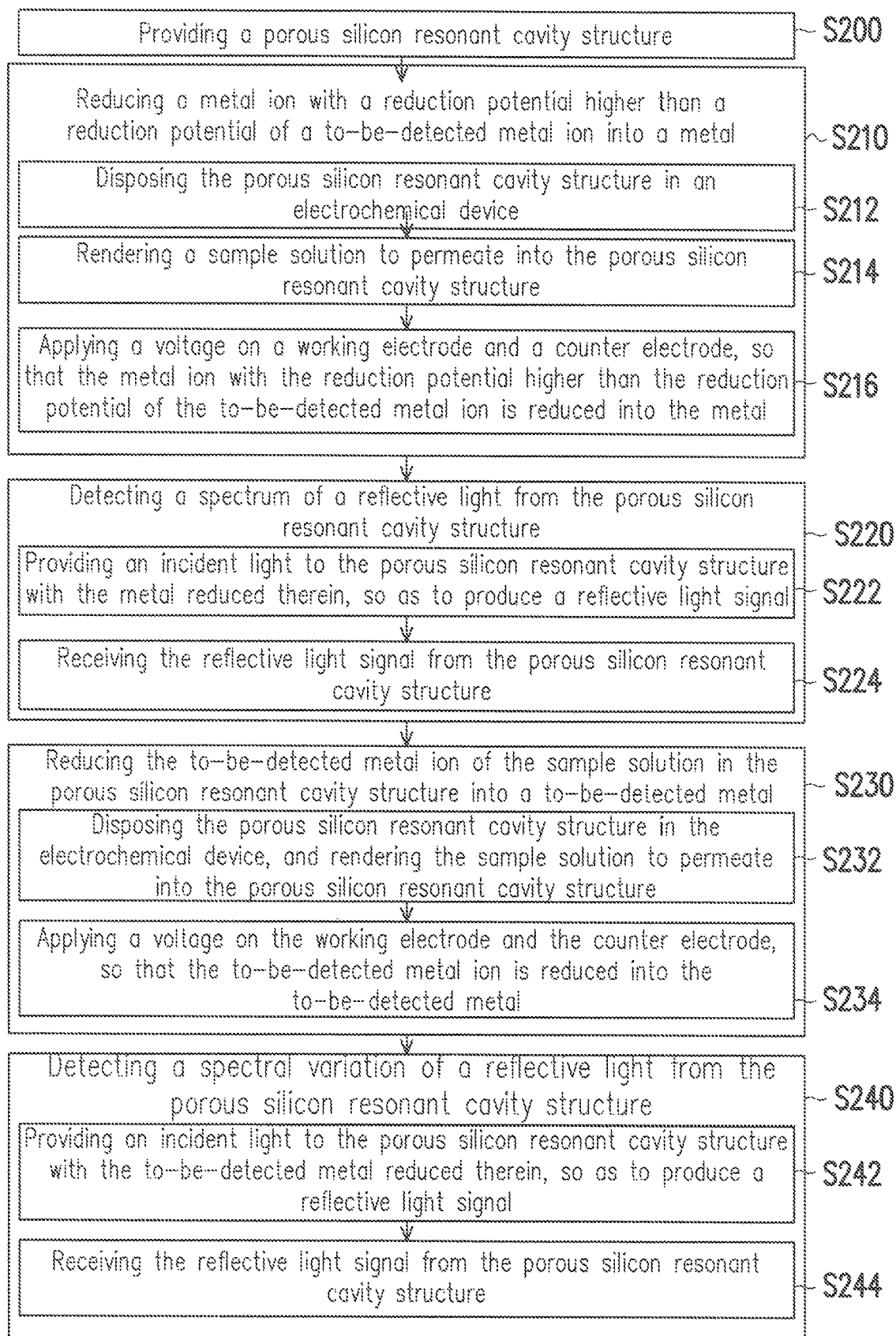
FIG. 5 is a flow chart illustrating the metal ion detection according to the second embodiment of the present invention.

FIG. 5 is a flow chart illustrating the metal ion detection according to the second embodiment of the present invention. In the embodiment, the porous silicon resonant cavity structure, electrochemical device, and the spectrum analyzer identical to the first embodiment is used to perform the metal ion detection. Therefore, the following embodiments use partial content of the foregoing embodiments, and omit the descriptions about the same technical content.

Referring to FIG. 5, the specific description of the steps of the metal ion detection are provided in the following paragraphs.

First, the step S200 is performed: the porous silicon resonant cavity structure is provided.

Then, the step S210 is performed: a metal ion with a reduction potential higher than a reduction potential of a to-be-detected metal ion is reduced into the metal. The step S210 can further include sub-steps S212, S214, S216. The sub-step S212 is performed: a porous silicon resonant cavity structure is disposed in an electrochemical device.

Then, the sub-step S214 is performed: a sample solution is rendered to permeate into the porous silicon resonant cavity structure. Specifically, the sample solution is injected into a reaction chamber of the electrochemical device, so that the sample solution covers the whole porous silicon resonant cavity structure and permeates into the porous silicon resonant cavity structure. In the embodiment, the sample solution includes a variety of metal ions.

Then, the sub-step S216 is performed: a voltage is applied on a working electrode and a counter electrode, so that the metal ion with the reduction potential higher than the reduction potential of the to-be-detected metal ion is reduced into the metal. The reduction potential of each kind of metal ions are different, and the higher the reduction potential of the metal ion, the easier the reduction of the metal ion into metal. Therefore, the metal ions with reduction potentials from high to low can be reduced gradually. The sample solution of the embodiment includes a variety of metal ions, therefore, before the to-be-detected metal ion is reduced into the to-be-detected metal, through applying voltage on the working electrode and the counter electrode, only the metal ion with the reduction potential higher than the reduction potential of the to-be-detected metal ion in the sample solution is reduced into metal, and the to-be-detected metal ion is not reduced into the to-be-detected metal. Furthermore, the reduced metal will be adsorbed on a surface and in the pore of the porous silicon resonant cavity structure.

For example, the sample solution includes Pb ion ($Pb^{2+}$), Ni ion ($Ni^{2+}$), and the target Cd ion ($Cd^{2+}$), wherein the reduction potential of the Pb ion (−0.13V) and the reduction potential of the Ni ion (−0.25V) are higher than the reduction potential of the Cd ion (−0.4V). Therefore, before the reduction of the Cd ion, the Ni ion and the Pb ion can be reduced into metal Ni and metal Pb first.

Thereafter, the step S220 is performed: a spectrum of a reflective light from the porous silicon resonant cavity structure is detected. The method of detecting the spectrum is in-situ detection or ex-situ detection. The step S220 can further include sub-steps S222, S224. The sub-step S222 is performed: an incident light is provided to the porous silicon resonant cavity structure with the metal reduced therein, so as to produce a reflective light signal. The wavelength of the incident light is 360 nm to 2400 nm, for example.

Then, the sub-step S224 is performed: the reflective light signal from the porous silicon resonant cavity structure is received, and the reflective light spectrum is displayed through a computer analysis. In the embodiment, the reflective light spectrum of the porous silicon resonant cavity structure injected with deionized water is used as a blank spectrum. Therefore, the concentration of the reduce metal can be calculated according to the sifted value of the spectrum (that is, the shifted value of the characteristic peak).

Then, the step S230 is performed: the to-be-detected metal ion of the sample solution in the porous silicon resonant cavity structure is reduced into a to-be-detected metal. The step S230 can further include sub-steps S232, S234. The sub-step S232 is performed: the porous silicon resonant cavity structure is disposed in the electrochemical device, and the sample solution is rendered to permeate into the porous silicon resonant cavity structure. Specifically, the porous silicon resonant cavity structure after the detection is put back into the electrochemical device, in the meanwhile, the sample solution covers the whole porous silicon resonant cavity structure and permeates into the porous silicon resonant cavity structure. The ex-situ detection is used as an example in the embodiment, therefore, the porous silicon resonant cavity structure needs to be disposed in the electrochemical device again. In another embodiment, the in-situ detection is performed, so that the step S232 is omitted. Furthermore, in another embodiment, the to-be-detected metal is reduced on another porous silicon resonant cavity structure. That is, two porous silicon resonant cavity structures are disposed in the electrochemical device, one is for filtering the metal ion with the reduction potential higher than that of the to-be-detected metal ion, the other is for reducing the to-be-detected metal ion and for the detection of the spectrum variation.

Then, the sub-step S234 is performed: a voltage is applied on the working electrode and the counter electrode, so that the to-be-detected metal ion is reduced into the to-be-detected metal. Specifically, the voltage is applied on the working electrode and the counter electrode through a potentiostat, so that the to-be-detected metal ion in the sample solution is reduced into the to-be-detected metal, and the reduced to-be-detected metal will be adsorbed on the surface and in the pores of the porous silicon resonant cavity structure.

Thereafter, the step S240 is performed: a spectral variation of the reflective light from the porous silicon resonant cavity structure is detected. The method of detecting the spectral variation is in-situ detection or ex-situ detection. The step S240 can further include sub-steps S242, S244. The sub-step S242 is performed: an incident light is provided to the porous silicon resonant cavity structure with the to-be-detected metal reduced therein, so as to produce a reflective light signal. The wavelength of the incident light is 360 nm to 2400 nm, for example.

Then, the sub-step S244 is performed: the reflective light signal from the porous silicon resonant cavity structure is received, and the reflective light spectral variation is displayed through the computer analysis. In the embodiment, because the metal ion with the reduction potential higher than the reduction potential of the to-be-detected metal ion has already been reduced into metal in the step S210, and the reflective light spectrum of the reduced metal described above is obtained in the step S220. Therefore, the concentration of the to-be-detected metal can be calculated according to the shifted value of the characteristic peak of the spectrum.

When the metal ion detection method described above is applied on heavy metal ion detection, under the condition of the sample solution containing various kind of heavy metal ions, because the reduction potentials of the heavy metals are different, the heavy metal ions with reduction potentials from high to low can be separated out due to the electrochemical reduction characteristics. The shifting phenomenon along with the separation of the heavy metal ion can also be observed in the spectrum, the effect of qualitative detection can be achieved through the electrochemical reduction potential, and the spectrum shifting value can determine the value of the heavy metal concentration.

It can be known from the above embodiment that because the porous silicon resonant cavity structure is a porous photonic crystal structure, and has high surface area, so the detection limit can be improved. In addition, the oscillating field of the photonic crystal can be used by the porous silicon resonant cavity structure to interact with the to-be-detected metal, so as to increase the detection sensitivity. Furthermore, in the embodiment, through the reduction of the to-be-detected metal ion in the porous silicon resonant cavity structure into the to-be-detected metal, the relatively greater change of the refractive index (relative to the change of the refractive index caused by the to-be-detected metal ion) can be caused, so that the signal of the reflective light can be increased and the detection limit can be improved.

In addition, the kind of the metal ions can be distinguished according to the reduction potential of the metal ion in the embodiment, and the concentration of the to-be-detected metal can be calculated through the spectral shifting value of reflective light of different metals (that is, the shifted value of the characteristic peak). That is, before the detection of the to-be-detected metal ion, only the metal ion with the reduction potential higher than the to-be-detected metal ion is needed to be reduced and detected for the reflective light spectrum thereof, and no additional process is needed to remove the non-to-be-detected metal ions. Therefore, it is beneficial to perform the target molecule selection, instant detection, and detection process simplification.

Hereinafter, experimental examples of the present disclosure are listed to describe the present invention more specifically. However, without departing from the spirit of the invention, the material, used method of the following experimental example can be adjusted appropriately. Accordingly, the scope of the present invention should not be limited by the experimental examples shown in the following paragraphs.

Experimental Example 1

In the experimental example 1, the metal ion detection equipment (including the porous silicon resonant cavity structure, electrochemical device, and the spectrum detecting device) of FIG. 1 is used and the metal ion detection is performed according to the metal ion detection steps illustrated in FIG. 4. The structure parameter of the porous silicon resonant cavity structure is illustrated as table 1. The spectrum detecting device is spectrum analyzer (model USB4000, Ocean Optics). The 1 ppb cadmium nitrate solution is used as sample solution, wherein the Cd ion is the to-be-detected metal ion.

TABLE 1

| | layer | refractive index | thickness (nm) |
|---|---|---|---|
| first bragg reflector | high refractive index layer | 5 | 1.63 | 90 |
| | low refractive index layer | 5 | 1.2 | 170 |
| second bragg reflector | high refractive index layer | 5 | 1.63 | 90 |
| | low refractive index layer | 5 | 1.2 | 170 |
| defect layer | — | 1 | 1.63 | 220 |

The metal ion detection steps are as follows: disposing the porous silicon resonant cavity structure into the electrochemical device, and injecting the sample solution into the reaction chamber of the electrochemical device, so that the sample solution covers the whole porous silicon resonant cavity structure and permeates into the porous silicon resonant cavity structure. The Cd ion of the sample solution in the porous silicon resonant cavity structure is reduced into metal Cd, and metal Cd will be adsorbed on the surface and in the pore of the porous silicon resonant cavity structure. An incident light of 360 nm to 2400 is provided to the porous silicon resonant cavity structure with metal Cd reduced therein through light source to produce the signal of the reflective light. The signal of the reflective light from the porous silicon resonant cavity structure is received, and the reflective light spectral variation is displayed through computer analysis.

Experimental Example 2

Experimental example 2 uses the method similar to the experimental example 1 to detect the metal ion. The difference lies in that the experimental example 2 uses the 10 ppb cadmium nitrate solution as sample solution.

Experimental Example 3

Experimental example 3 uses the method similar to the experimental example 1 to detect the metal ion. The difference lies in that the experimental example 3 uses the 100 ppb cadmium nitrate solution as sample solution.

Experimental Example 4

Experimental example 4 uses the method similar to the experimental example 1 to detect the metal ion. The difference lies in that the experimental example 4 uses the 1000 ppb cadmium nitrate solution as sample solution.

Control Group 1

In the control group 1, the reflective light spectrum of the porous silicon resonant cavity structure injected with deionized water is used as the blank spectrum.

Comparative Example 1

The comparative example 1 uses the method similar to experimental example 1. The difference lies in that 5% cadmium nitrate solution is used as sample solution in the comparative example 1, and the electrochemical reduction reaction is not performed on the sample solution in the comparative example 1 (that is, the Cd ion of the sample solution in the porous silicon resonant cavity structure is not reduced into metal Cd).

Comparative Example 2

Comparative example 2 uses the method similar to the comparative example 1 to detect the metal ion. The difference lies in that the comparative example 2 uses the 10% cadmium nitrate solution as sample solution.

Comparative Example 3

Comparative example 3 uses the method similar to the comparative example 1 to detect the metal ion. The difference lies in that the comparative example 3 uses the 15% cadmium nitrate solution as sample solution.

Comparative Example 4

Comparative example 4 uses the method similar to the comparative example 1 to detect the metal ion. The difference lies in that the comparative example 4 uses the 20% cadmium nitrate solution as sample solution.

Comparative Example 5

Comparative example 5 uses the method similar to the comparative example 1 to detect the metal ion. The difference lies in that the comparative example 5 uses the 25% cadmium nitrate solution as sample solution.

Control Group 2

In the control group 2, the reflective light spectrum of the porous silicon resonant cavity structure injected with deionized water is used as the blank spectrum.

Figure 6A:
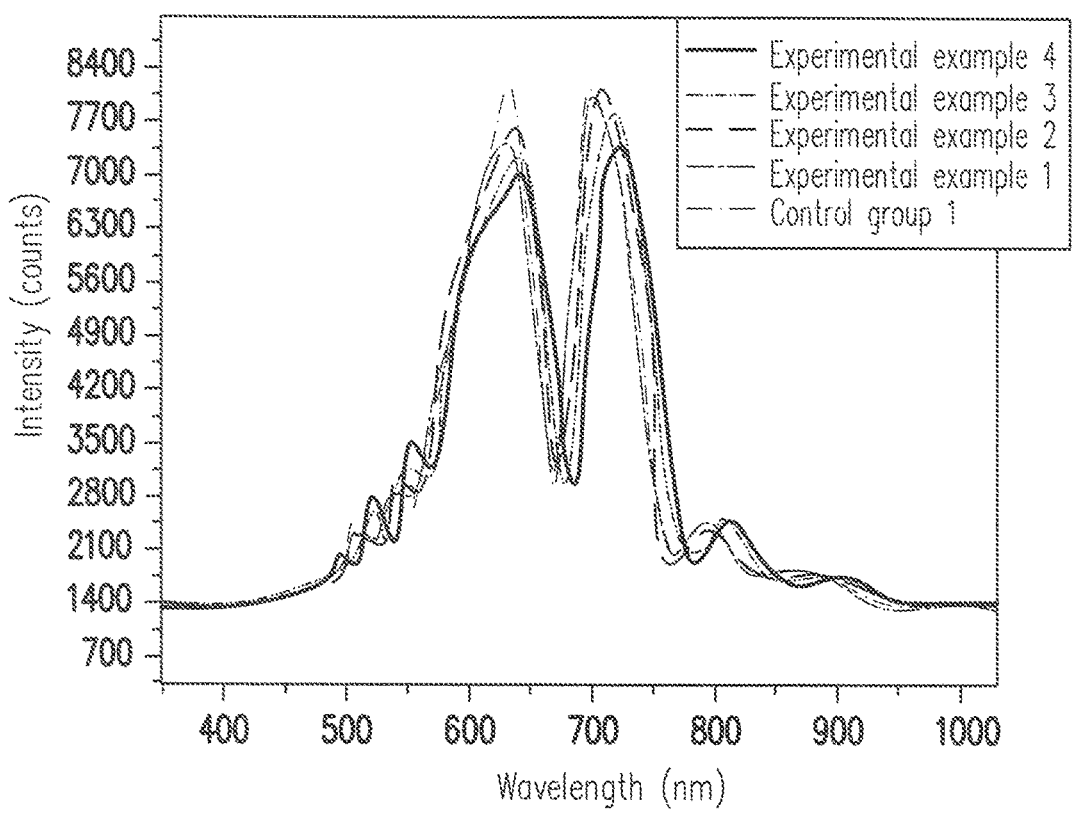
FIG. 6A is the reflective light spectrum of the experiment example 1 to experiment example 4 and the control group 1.
Figure 6B:
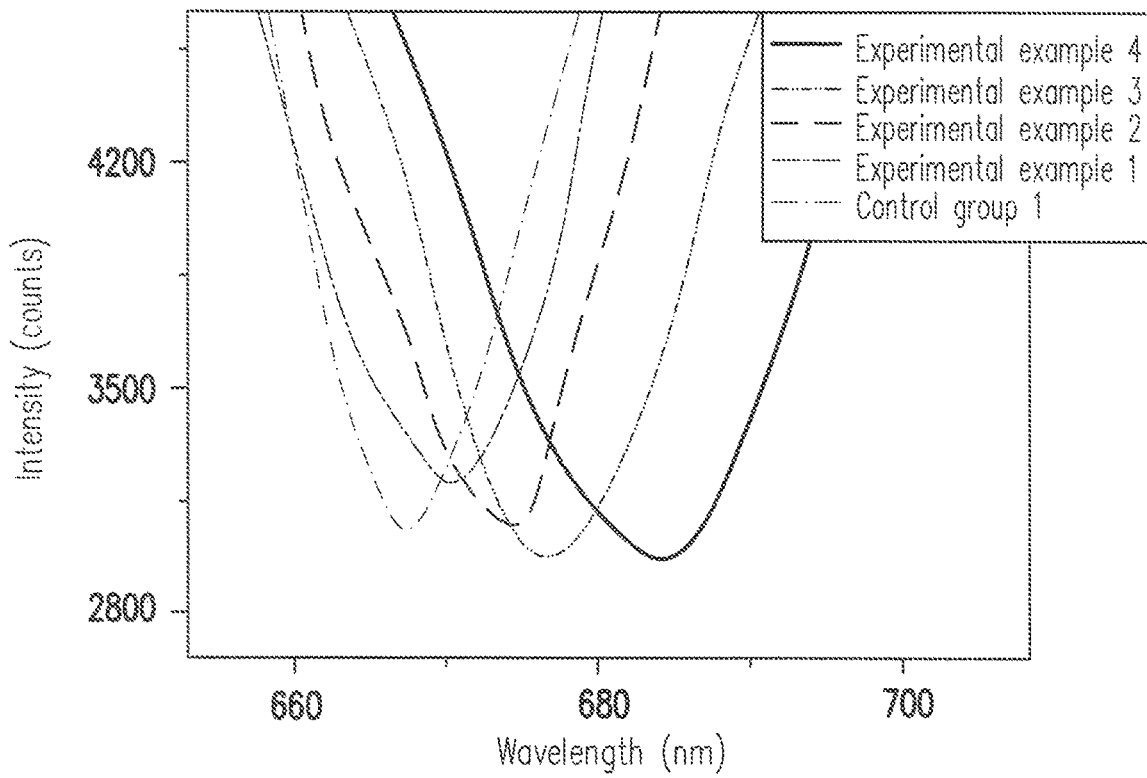
FIG. 6B is the partially enlarged view of the characteristic peak of the reflective light spectrum of the experiment example 1 to experiment example 4 and the control group 1.
Figure 6C:
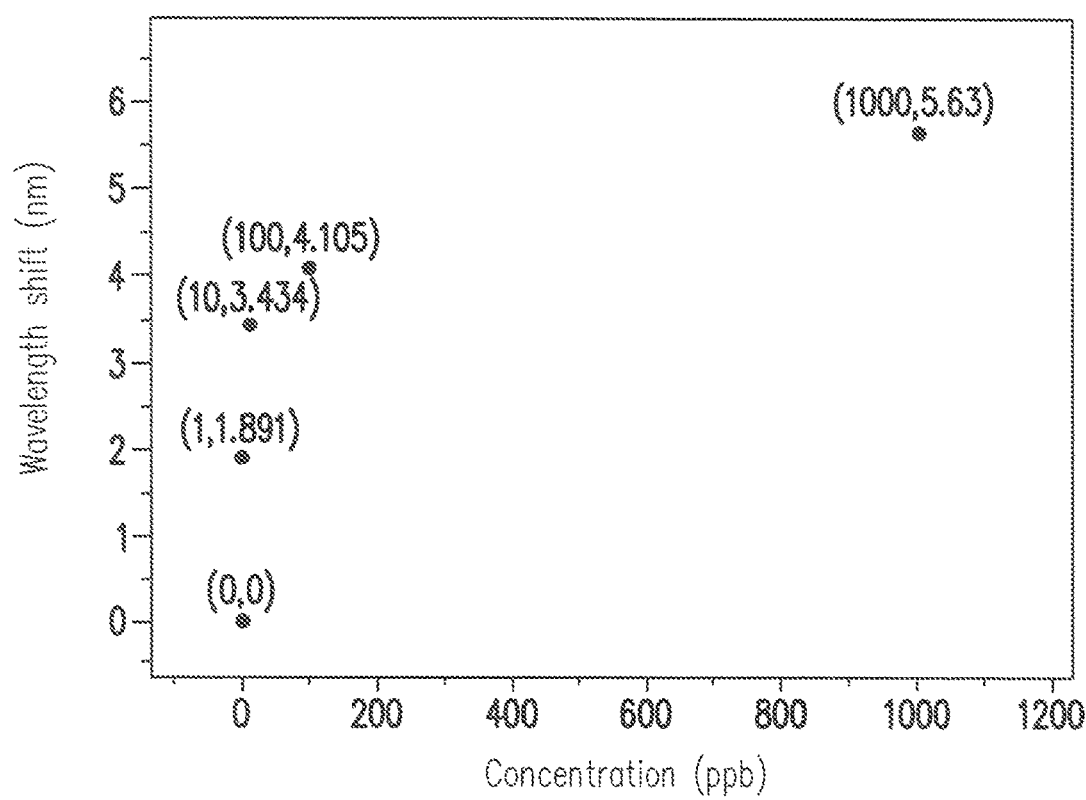
FIG. 6C is the correlation diagram illustrating the red shift of the characteristic peak corresponding to the cadmium nitrate concentration of the experiment example 1 to experiment example 4 and the control group 1.

FIG. 6A is the reflective light spectrum of the experiment example 1 to experiment example 4 and the control group 1. FIG. 6B is the partially enlarged view of the characteristic peak of the reflective light spectrum of the experiment example 1 to experiment example 4 and the control group 1. FIG. 6C is the correlation diagram illustrating the red shift of the characteristic peak corresponding to the cadmium nitrate concentration of the experiment example 1 to experiment example 4 and the control group 1.

As illustrated in FIG. 6A to 6C, when cadmium nitrate solution enters the porous silicon resonant cavity structure and reduces the Cd ion in the cadmium nitrate solution into metal Cd through the electrochemical device, a remarkable change on the overall refractive index is caused, so that a red shift is induced on the characteristic peak. Also, it can be known from experiment example 1 to experiment example 4 that in the concentration range of 1 ppb to 1000 ppb, the red shift of the characteristic peak is increased with the increase of the concentration of the cadmium nitrate. In addition, after the reduction of the Cd ion of the sample solution containing 1 ppb cadmium nitrate (experiment example 1) into metal Cd, the characteristic peak thereof red shifts 1.891 nm due to the increase of the refractive index, and the detection limit calculated is less than 1 ppb accordingly.

Figure 7A:
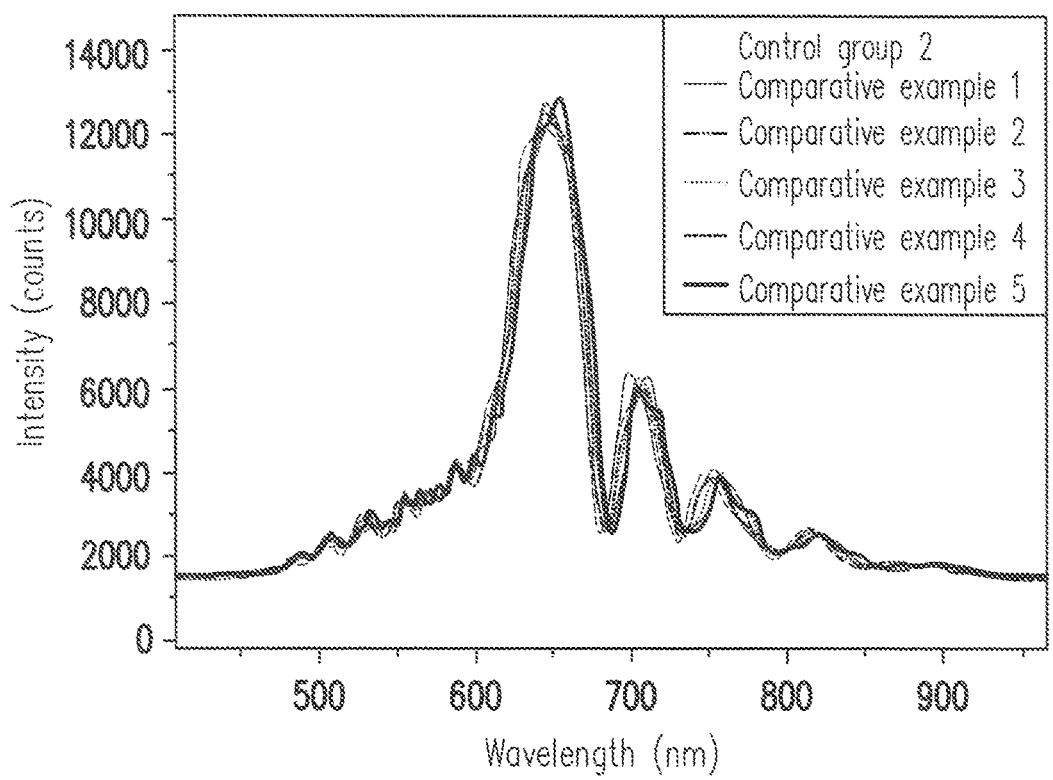
FIG. 7A is the reflective light spectrum of the comparative example 1 to comparative example 5 and the control group 2.
Figure 7B:
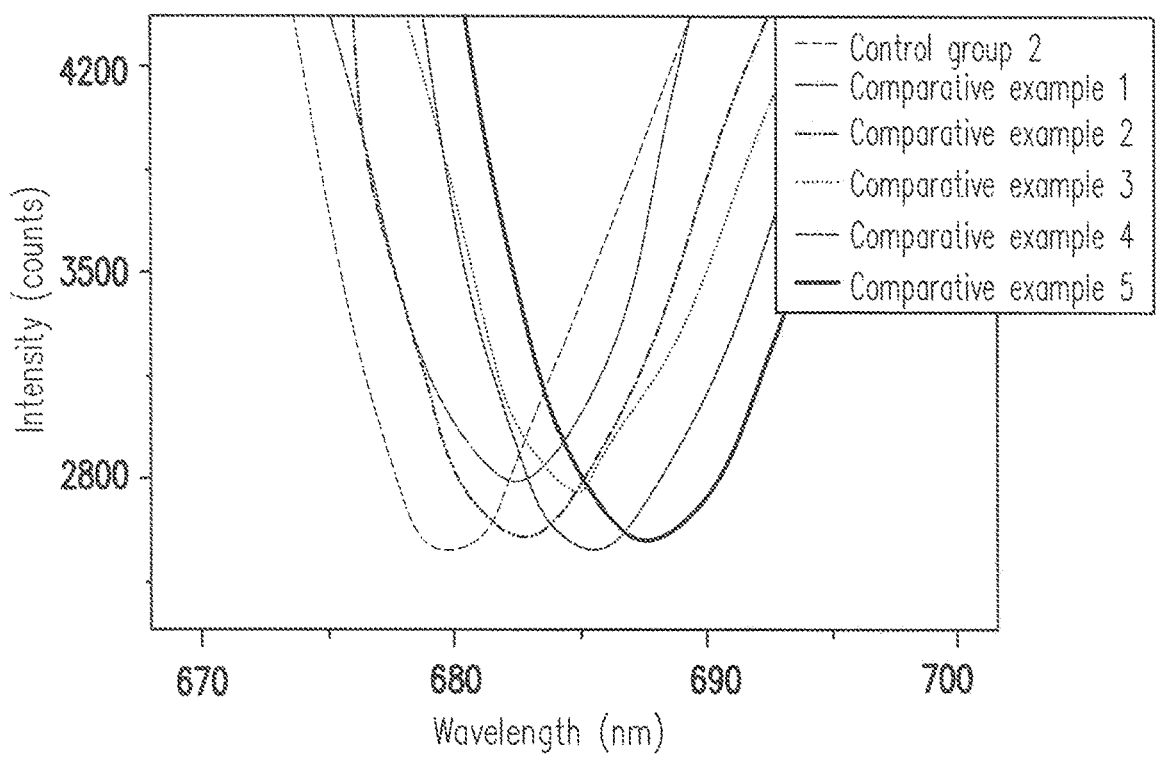
FIG. 7B is the partially enlarged view of the characteristic peak of the reflective light spectrum of the comparative example 1 to comparative example 5 and the control group 2.
Figure 7C:
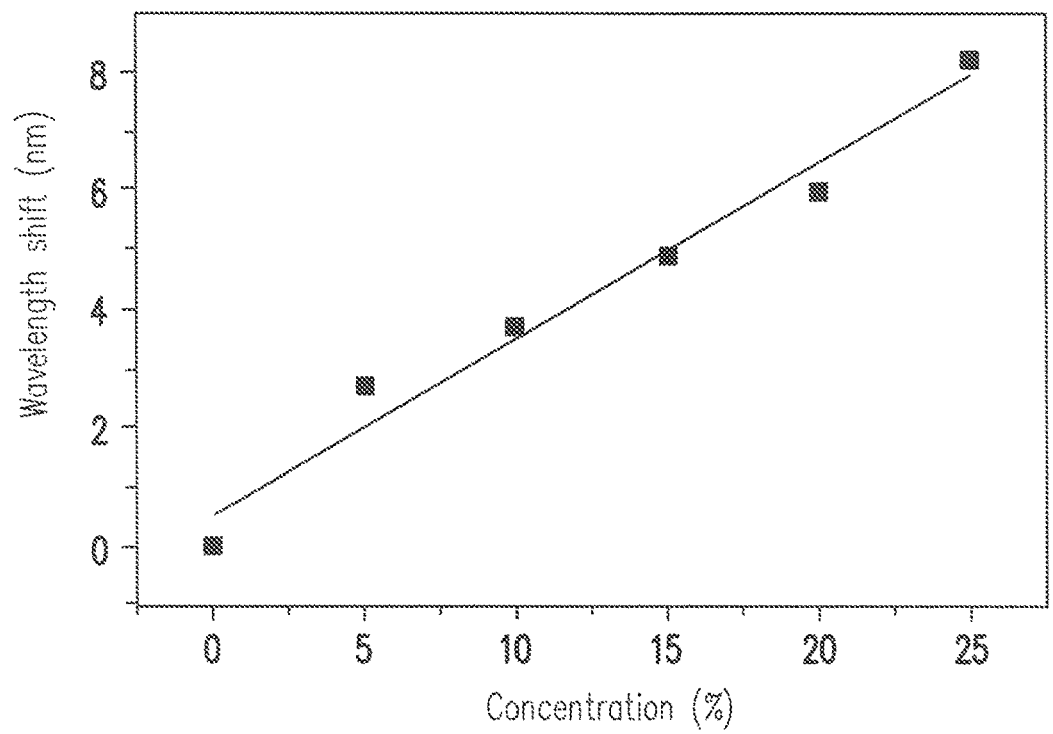
FIG. 7C is the correlation diagram illustrating the red shift of the characteristic peak corresponding to the cadmium nitrate concentration of the comparative example 1 to comparative example 5 and the control group 2.

FIG. 7A is the reflective light spectrum of the comparative example 1 to comparative example 5 and the control group 2. FIG. 7B is the partially enlarged view of the characteristic peak of the reflective light spectrum of the comparative example 1 to comparative example 5 and the control group 2. FIG. 7C is the correlation diagram illustrating the red shift of the characteristic peak corresponding to the cadmium nitrate concentration of the comparative example 1 to comparative example 5 and the control group 2.

As illustrated in FIG. 7A to 7C, when cadmium nitrate solution enters the porous silicon resonant cavity structure, a change on the overall refractive index is caused, so that a red shift is induced on the characteristic peak. In addition, it can be known from comparative example 1 to comparative example 5 that in the concentration range of 5% to 25%, with the increase of the concentration of cadmium nitrate, the red shift of the characteristic peak is also increased, wherein after the sample solution (comparative example 1) containing 5% cadmium nitrate entered into the porous silicon resonant cavity structure, the characteristic peak thereof red shifts 4.3 nm due to the increase of the refractive index, and the calculated detection limit is about 34000 ppm accordingly.

It can be known from the results above that compared to the comparative example 1 to comparative example 5, because the Cd ion of the cadmium nitrate solution in the porous silicon resonant cavity structure is reduced into metal Cd in the experiment example 1 to experiment example 4, and the reduction of the liquid Cd ion into the solid metal Cd will cause a relatively great change of the refractive index, therefore, the detection limit can be improved (can be smaller than 1 ppb).

Based on the above, in the metal ion detection equipment and method provided by the present invention, through the reduction of the to-be-detected metal ion in the porous silicon resonant cavity structure into the to-be-detected metal, the relatively greater change of the refractive index can be caused, so that the detection limit can be improved.

In addition, compared to the conventional metal ion detector (like IPC-MS, FLAA, etc) and the analysis process, in the metal ion detection equipment and method provided by the present invention, metal ion can be selected according to the reduction potential of the metal ion. Therefore, no additional process is needed to remove the non-to-be-detected metal ion in the sample solution, so that it is benefit to perform target molecule selection, instant detection and detection process simplification.

Furthermore, the porous silicon resonant cavity structure in the metal ion detection equipment of the invention has the advantage such as high specific surface area and high sensitivity, also, the production thereof is easy, and the cost thereof is low.

And, the present invention can be applied on the pollution controlling of the wastewater of the factory, the instant detection can be performed on the wastewater, so that the detection cost and analysis time is decreased. In addition, the present invention can also be applied on the agriculture and the aquaculture, the analysis on the water can be performed so that whether the water is polluted by the heavy metal is determined.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. A metal ion detection equipment, comprising:
   a porous silicon resonant cavity structure, wherein a sample solution permeates into the porous silicon resonant cavity structure;
   an electrochemical device, reducing a to-be-detected metal ion of the sample solution in the porous silicon resonant cavity structure into a to-be-detected metal, wherein the electrochemical device comprises:
   a reaction chamber, configured to load the sample solution;
   a working electrode and a counter electrode, disposed in the reaction chamber, wherein the porous silicon resonant cavity structure is disposed on the working electrode; and
   a potentiostat, connected to the working electrode and the counter electrode; and
   a spectrum detecting device, detecting a spectral variation of a reflective light from the porous silicon resonant cavity structure.

2. The metal ion detection equipment according to claim 1, wherein the porous silicon resonant cavity structure comprises a first bragg reflector, a second bragg reflector, and a defect layer located between the first bragg reflector and the second bragg reflector, wherein the first bragg reflector and the second bragg reflector both comprise a plurality of low refractive index layers and a plurality of high refractive index layers, and the low refractive index layer and the high refractive index layer are arranged alternately.

3. The metal ion detection equipment according to claim 2, wherein a thickness of the low refractive index layer is 100 nm to 200 nm.

4. The metal ion detection equipment according to claim 2, wherein a thickness of the high refractive index layer is 50 nm to 100 nm.

5. The metal ion detection equipment according to claim 2, wherein a ratio of a thickness of the defect layer to a thickness of the high refractive index layer is 1.5 to 2.5.

6. The metal ion detection equipment according to claim 2, wherein a refractive index of the low refractive index layer is 1.1 to 1.3.

7. The metal ion detection equipment according to claim 2, wherein a refractive index of the high refractive index layer is 1.5 to 1.7.

8. The metal ion detection equipment according to claim 2, wherein a refractive index of the defect layer is 1.5 to 1.7.

9. The metal ion detection equipment according to claim 1, wherein the electrochemical device further comprises a reference electrode, and the reference electrode disposed in the reaction chamber and connected to the potentiostat.

10. A metal ion detection method, comprising:
reducing a to-be-detected metal ion of a sample solution in a porous silicon resonant cavity structure into a to-be-detected metal, wherein an electrochemical device is configured to reduce the to-be-detected metal ion into the to-be-detected metal, and the electrochemical device comprises:
a reaction chamber, configured to load the sample solution;
a working electrode and a counter electrode, disposed in the reaction chamber, wherein the porous silicon resonant cavity structure is disposed on the working electrode; and
a potentiostat, connected to the working electrode and the counter electrode; and
detecting a spectral variation of a reflective light from the porous silicon resonant cavity structure.

11. The metal ion detection method according to claim 10, wherein the porous silicon resonant cavity structure comprises a first bragg reflector, a second bragg reflector, and a defect layer located between the first bragg reflector and the second bragg reflector, wherein the first bragg reflector and the second bragg reflector both comprise a plurality of low refractive index layers and a plurality of high refractive index layers, and the low refractive index layer and the high refractive index layer are arranged alternately.

12. The metal ion detection method according to claim 10, wherein the sample solution comprises a variety of metal ions, and before the to-be-detected metal ion is reduced into the to-be-detected metal, the metal ion detection method further comprises using the electrochemical device to reduce a metal ion with a reduction potential higher than a reduction potential of the to-be-detected metal ion into a metal.

13. The metal ion detection method according to claim 12, wherein the step of reducing the metal ion with the reduction potential higher than the reduction potential of the to-be-detected metal ion into the metal comprises:
rendering the sample solution to permeate into the porous silicon resonant cavity structure; and
applying a voltage on the working electrode and the counter electrode, so that the metal ion with the reduction potential higher than the reduction potential of the to-be-detected metal ion is reduced into the metal.

14. The metal ion detection method according to claim 10, wherein the step of reducing the to-be-detected metal ion of the sample solution in the porous silicon resonant cavity structure into the to-be-detected metal comprises:
rendering the sample solution to permeate into the porous silicon resonant cavity structure; and
applying a voltage on the working electrode and the counter electrode, so that the to-be-detected metal ion is reduced into the to-be-detected metal.

15. The metal ion detection method according to claim 12, wherein after the metal ion with the reduction potential higher than the reduction potential of the to-be-detected metal ion is reduced into the metal, and before the to-be-detected metal ion is reduced into the to-be-detected metal, the metal ion detection method further comprises detecting a spectrum of the reflective light from the porous silicon resonant cavity structure.

16. The metal ion detection method according to claim 10, wherein a spectrum analyzer is configured to detect the spectral variation.

17. The metal ion detection method according to claim 10, wherein the step of detecting the spectral variation of the reflective light from the porous silicon resonant cavity structure comprises:
providing an incident light to the porous silicon resonant cavity structure with the to-be-detected metal reduced therein, so as to produce a reflective light signal; and
receiving the reflective light signal from the porous silicon resonant cavity structure.

18. The metal ion detection method according to claim 10, wherein the method of detecting the spectral variation is an in-situ detection or an ex-situ detection.

* * * * *